(12) United States Patent
Liang et al.

(10) Patent No.: US 11,510,905 B1
(45) Date of Patent: Nov. 29, 2022

(54) PLEUROMUTILIN (E)-4-(1-IMIDAZOYLMETHYL)CINNAMIC ACID ESTER WITH ANTI-DRUG RESISTANT BACTERIA ACTIVITY AND A METHOD OF PREPARING THE SAME

(71) Applicants: Chengyuan Liang, Xi'an (CN); Wenjing Yang, Xi'an (CN); Qianqian Zhao, Xi'an (CN); Liang Xin, Xi'an (CN); Jingyi Li, Xi'an (CN); Dan Yang, Xi'an (CN); Ruina Bian, Xi'an (CN); Jie Zhang, Xi'an (CN); Yuqing Zhao, Xi'an (CN); Han Li, Xi'an (CN); Bin Tian, Xi'an (CN); Yongbo Wang, Xi'an (CN); Liang Qi, Xi'an (CN); Gennian Mao, Xi'an (CN)

(72) Inventors: Chengyuan Liang, Xi'an (CN); Wenjing Yang, Xi'an (CN); Qianqian Zhao, Xi'an (CN); Liang Xin, Xi'an (CN); Jingyi Li, Xi'an (CN); Dan Yang, Xi'an (CN); Ruina Bian, Xi'an (CN); Jie Zhang, Xi'an (CN); Yuqing Zhao, Xi'an (CN); Han Li, Xi'an (CN); Bin Tian, Xi'an (CN); Yongbo Wang, Xi'an (CN); Liang Qi, Xi'an (CN); Gennian Mao, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 60 days.

(21) Appl. No.: 17/239,583

(22) Filed: Apr. 24, 2021

(51) Int. Cl.
  *C07D 233/60* (2006.01)
  *A61K 31/4164* (2006.01)
  *A61P 31/04* (2006.01)

(52) U.S. Cl.
  CPC .......... *A61K 31/4164* (2013.01); *A61P 31/04* (2018.01); *C07D 233/60* (2013.01)

(58) Field of Classification Search
  CPC .... C07D 233/60; A61K 31/4164; A61P 31/04
  See application file for complete search history.

(56) References Cited

PUBLICATIONS

Deng et al., Arch Pharm Chem Life Sci. 2019;352:e1800266.*

* cited by examiner

*Primary Examiner* — Alicia L Otton

(57) ABSTRACT

A compound with anti-drug resistant bacteria activity having the following formula (I):

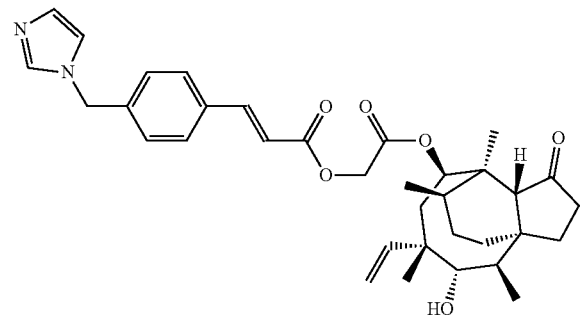

is disclosed. The methods of preparing the compound of formula (I) are also disclosed.

17 Claims, 2 Drawing Sheets

PLEUROMUTILIN (E)-4-(1-IMIDAZOYLMETHYL)CINNAMIC ACID ESTER WITH ANTI-DRUG RESISTANT BACTERIA ACTIVITY AND A METHOD OF PREPARING THE SAME

FIELD OF THE INVENTION

The present invention relates to the field of medicinal chemistry, and in particular, to pleuromutilin (E)-4-(1-imidazoylmethyl)cinnamic acid ester with anti-drug resistant bacteria activity and a method of preparing the same.

BACKGROUND OF THE INVENTION

With the widespread use of antimicrobials and the increase in various invasive operations, the spectrum of clinical infection pathogens continues to change, and the drug resistance of bacteria continues to increase. The infection rate of various drug-resistant bacteria and the mortality rate of patients have increased year by year. Here comes a huge challenge. The problem of drug-resistant bacteria has become very prominent, and solving the problem of bacterial drug resistance has become a top priority.

Pleuromutilin (compound of formula II) is an antibiotic produced by submerged culture of higher fungi *pleurotus* pleurotusmutilis and *pleurotus* passeckeranius. It is a diterpene compound. with a molecular formula of $C_{22}H_{34}O_5$, a molecular weight of 378.51, and a melting point of 167-168° C. Pleuromutilin and its derivatives can inhibit bacterial protein synthesis at the ribosome level, and have unique effects on many Gram-positive bacteria and *Mycoplasma* infections.

(E)-4-(1-imidazoylmethyl)cinnamic acid (CAS: 82571-53-7) (compound of formula IV), namely Ozagrel, can inhibit TXA2 synthase, has anti-platelet aggregation and relieves vasospasm. It is clinically used for the improvement of vasospasm and the symptoms of cerebral ischemia after subarachnoid hemorrhage surgery, and for the treatment of acute thrombotic cerebral infarction and dyskinesia accompanying cerebral infarction.

The invention modifies pleuromutilin through (E)-4-(1-imidazoyl-methyl)cinnamic acid structure to obtain a pleuromutilin (E)-4-(1-imidazoylmethyl)cinnamic acid ester. Preliminary antibacterial activity experiment shows that the compound has excellent antibacterial activity and has high medical research and application value in the treatment of infectious diseases caused by multi-drug-resistant bacteria.

SUMMARY OF THE INVENTION

In one embodiment, the present invention provides a compound with anti-drug resistant bacteria activity having the following formula (I):

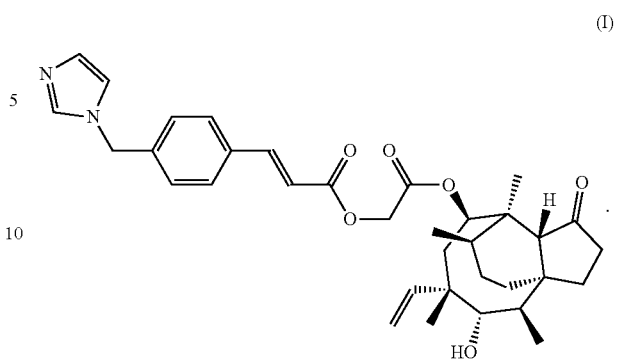

In another embodiment, a method of preparing the compound of formula (I) includes: reacting a compound of formula (II) with a compound of formula (III) to obtain the compound of formula (I):

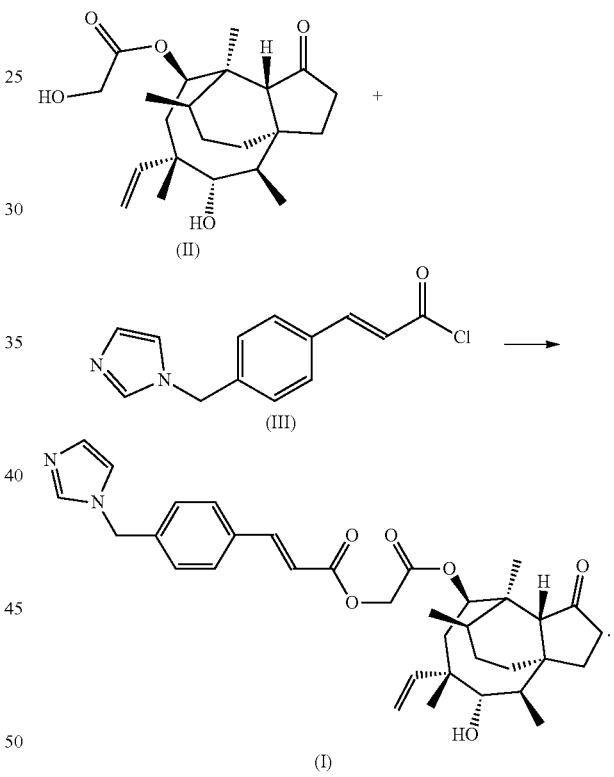

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; heating the reaction mixture at 20-60° C. for 3-6 hours; extracting the reaction mixture with ethyl acetate to obtain a crude product; and purifying the crude product on a silica gel fresh chromatography column with dichloromethane and methanol as an eluent to obtain the compound of formula (I).

In another embodiment, the organic solvent is toluene, dichloromethane or N,N-dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 25° C.

In another embodiment, the reaction mixture is heated for 5 hours.

In another embodiment, the eluent is dichloromethane:methanol=10:1.

In another embodiment, a method of preparing the compound of formula (I) includes: reacting a compound of formula (II) with a compound of formula (IV) to obtain the compound of formula (I):

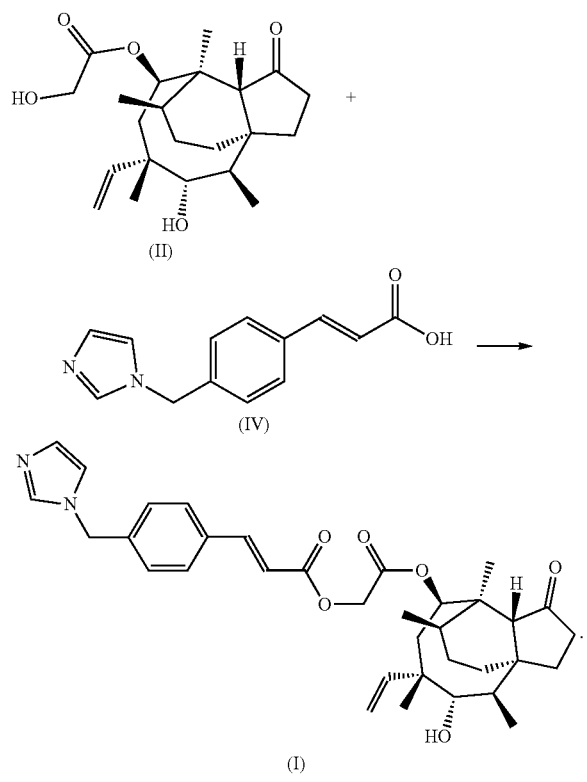

In another embodiment, the reaction of the compound of formula (II) with the compound of formula (IV) included the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (IV) to the reactor to form a reaction mixture; heating the reaction mixture at 20-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate, 1-hexyl-3-methylimidazolium tetrafluoroborate or 1-butyl-3-methylimidazolium tetrafluoroborate ([BMIM][BF4]).

In another embodiment, the ionic liquid is the ionic liquid is 1-butyl-3-methylimidazolium tetrafluoroborate.

In another embodiment, the compound of formula (II) and the compound (IV) have a molar ratio of 1:1 to 1:1.3.

In another embodiment, the molar ratio of the compound of formula (II) and the compound of formula (IV) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
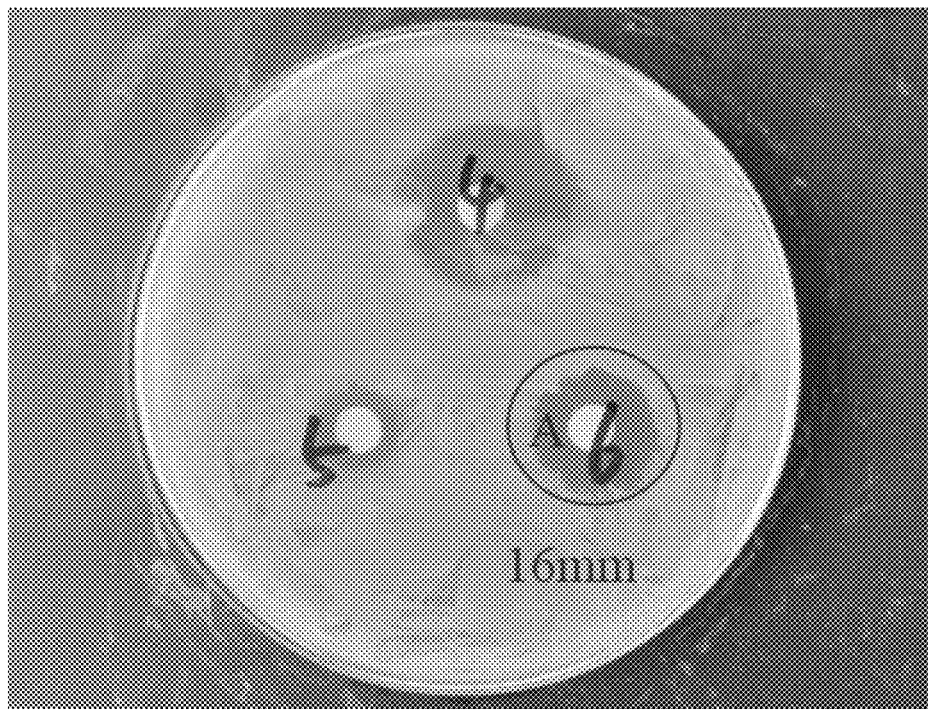
FIG. 1 shows the in vitro antibacterial activity of pleuromutilin (E)-4-(1-imidazoylmethyl)cinnamic acid ester against drug-resistant bacteria MARS 18-171.

Reference will now be made in detail to embodiments of the present invention, example of which is illustrated in the accompanying drawings. The following examples illustrate the present invention, but the present invention is not limited to the following examples.

Example 1

Preparation of pleuromutilin (E)-4-(1-imidazoylmethyl)cinnamic acid ester (Compound of Formula I) ((E)-2-(((3aS,4R,5S,6S,8R,9R,9aR,12R)-5-hydroxy-4,6,9,12-tetramethyl-1-oxo-6-vinyldecahydro-3a,9-propanocyclopenta[8]annulen-8-yl)oxy)-2-oxoethyl-3-(4-((1H-imidazol-1-yl)methyl)phenyl)acrylate)

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 177.2 mg (0.72 mmol) of (E)-4-(1-imidazoylmethyl)cinnamic acid chloride (compound of formula III) was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 274.6 mg of the title compound, a yield of 76.9%.

¹H-NMR (400 MHz, Chloroform-d) δ (ppm): 8.05 (1H, s), 7.68 (2H, d), 7.54 (2H, d), 7.22 (2H, d), 7.16 (1H, d), 6.95 (1H, d), 6.56 (2H, t), 5.86 (1H, t), 5.40 (2H, d), 5.20 (2H, s), 4.75 (1H, t), 4.09 (1H, t), 3.41 (1H, d), 2.99 (1H, s), 2.25 (4H, t), 1.71-1.39 (11H, t), 1.18 (3H, s), 0.93 (3H, s), 0.82 (3H, s); ¹³C-NMR (100 MHz, Chloroform-d) δ (ppm): 216.8, 166.7, 165.7, 162.5, 145.1, 138.4. 129.6, 127.8, 117.6, 117.3, 74.6, 69.8, 58.1, 45.4, 41.9, 36.0, 30.4, 24.8, 16.6, 14.8, 11.4, 8.6.

Example 2

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 159.9 mg (0.65 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 234.6 mg of the title compound, a yield of 65.7%.

Example 3

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 191.9 mg (0.78 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 242.8 mg of the title compound, a yield of 68.0%.

Example 4

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 191.9 mg (0.78 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 30° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 229.6 mg of the title compound, a yield of 64.3%.

Example 5

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 159.9 mg (0.65 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 30° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 235.1 mg of the title compound, a yield of 65.9%.

Example 6

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 159.9 mg (0.65 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 40° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 251.3 mg of the title compound, a yield of 70.4%.

Example 7

Preparation of pleuromutilin
(E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 209.2 mg (0.85 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 244.5 mg of the title compound, a yield of 68.5%.

Example 8

Preparation of pleuromutilin (E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 209.2 mg (0.85 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 230.3 mg of the title compound, a yield of 64.5%.

Example 9

Preparation of pleuromutilin (E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 177.2 mg (0.72 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 238.9 mg of the title compound, a yield of 66.9%.

Example 10

Preparation of pleuromutilin (E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 177.2 mg (0.72 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 222.4 mg of the title compound, a yield of 62.3%.

Example 11

Preparation of pleuromutilin (E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 159.9 mg (0.65 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=10:1 as eluent, and the eluent was combined and concentrated under reduced pressure to obtain 218.0 mg of the title compound, a yield of 61.1%.

Example 12

Preparation of pleuromutilin (E)-4-(1-imidazoylmethyl)cinnamic acid ester

In a 100 mL three-necked flask, 246.0 mg (0.65 mmol) of pleuromutilin and 6.1 mg (0.06 mmol) of triethylamine were dissolved in 25 mL of dichloromethane under nitrogen atmosphere. 177.2 mg (0.72 mmol) of (E)-4-(1-imidazoylmethyl)cinnamic acid chloride was dissolved in 10 mL of dichloromethane, and added dropwise to the reaction mixture by a separatory funnel. After the completion of the dropwise addition, the reaction was carried out at 20° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with dichloromethane:methanol=8:1 as eluent, and the eluent was combined and concentrated under reduced pressure to obtain 231.2 mg of the title compound, a yield of 64.8%.

Example 13

Preparation of pleuromutilin (E)-4-(1-imidazoylmethyl)cinnamic acid ester

In a 250 mL three-necked flask, 246.0 mg (0.65 mmol) of pleuromutilin, 164.0 mg (0.72 mmol) of (E)-4-(1-imidazoylmethyl)cinnamic acid and 12.0 mg (0.007 mmol) silicomolybdic acid were dissolved in 150 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 308.5 mg of the title compound, a yield of 86.42%.

Example 14

Preparation of pleuromutilin (E)-4-(1-imidazoylmethyl)cinnamic acid ester

In a 250 mL three-necked flask, 246.0 mg (0.65 mmol) of pleuromutilin, 178.0 mg (0.78 mmol) of (E)-4-(1-imidazoylmethyl)cinnamic acid and 12.0 mg (0.007 mmol) silicomolybdic acid were dissolved in 150 mL of 1-butyl-3-methylimidazolium tetrafluoroborate under nitrogen atmosphere. After full dissolution, the temperature of the reaction mixture was raised to 30° C. and the reaction was carried out for 8 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 283.6 mg of the title compound, a yield of 79.45%.

Example 15

Preparation of pleuromutilin (E)-4-(1-imidazoylmethyl)cinnamic acid ester

In a 250 mL three-necked flask, 246.0 mg (0.65 mmol) of pleuromutilin, 148.0 mg (0.65 mmol) of (E)-4-(1-imidazoylmethyl)cinnamic acid and 12.0 mg (0.007 mmol) silicomolybdic acid were dissolved in 150 mL of 1-butyl-3-methylimidazolium tetrafluoroborate under nitrogen atmosphere. After full dissolution, the temperature of the reaction mixture was raised to 40° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 279.9 mg of the title compound, a yield of 78.42%.

Example 16

Preparation of pleuromutilin (E)-4-(1-imidazoylmethyl)cinnamic acid ester

In a 250 mL three-necked flask, 246.0 mg (0.65 mmol) of pleuromutilin, 164.0 mg (0.72 mmol) of (E)-4-(1-imidazoylmethyl)cinnamic acid and 12.0 mg (0.007 mmol) silicomolybdic acid were dissolved in 150 mL of 1-butyl-3-methylimidazolium tetrafluoroborate under nitrogen atmosphere. After full dissolution, the temperature of the reaction mixture was raised to 40° C. and the reaction was carried out for 8 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 276.7 mg of the title compound, a yield of 77.52%.

Example 17

Antibacterial Activity Test of the Compounds of the Invention

The antimicrobial efficacy was determined by a paper diffusion method drug sensitivity test.

Experimental strains: multi-resistant *Staphylococcus aureus* 171, multi-resistant *Staphylococcus aureus* 222, multi-resistant *Staphylococcus aureus* 575. The experimental strains were identified by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was vancomycin (30 μg/tablet); the test drugs were pleuromutilin (E)-4-(1-imidazoyl-methyl)cinnamic acid ester (30 μg/tablet).

Reagents: LB agar medium, LA broth medium, dichloromethane.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 15^8$ CFU/mL). A bacterial suspension is obtained.

Paper Diffusion Method Drug Sensitivity Test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and to evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone ≥17 mm, sensitive; the inhibition zone of 15 mm-16 mm, intermediary; the inhibition zone ≥14 mm, drug resistance.

Figure 2:
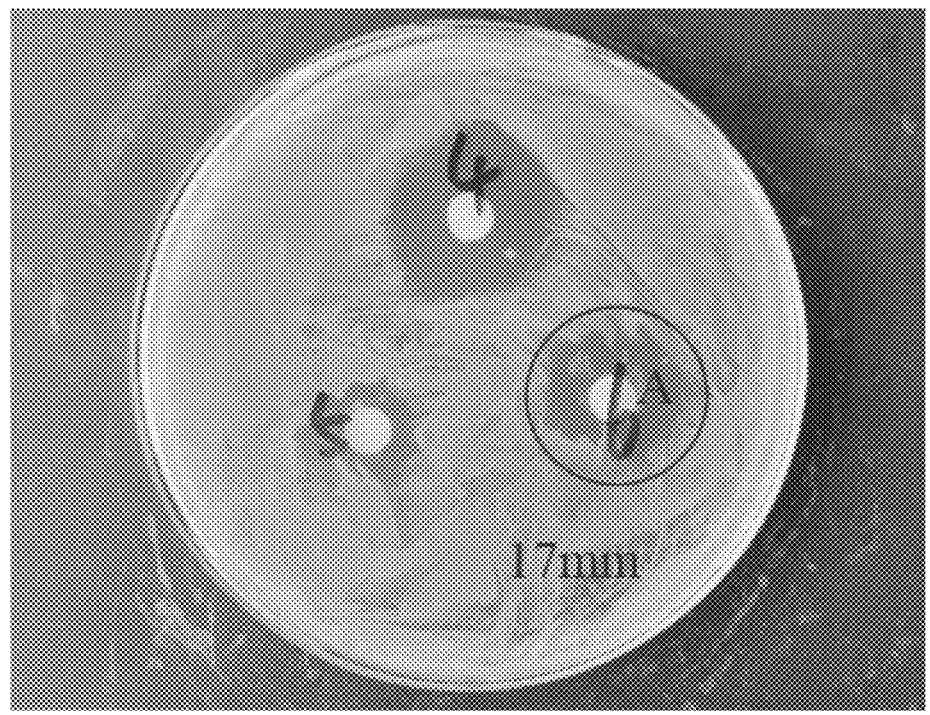
FIG. 2 shows the in vitro antibacterial activity of pleuromutilin (E)-4-(1-imidazoylmethyl)cinnamic acid ester against drug-resistant bacteria MRSA 18-222.
Figure 3:
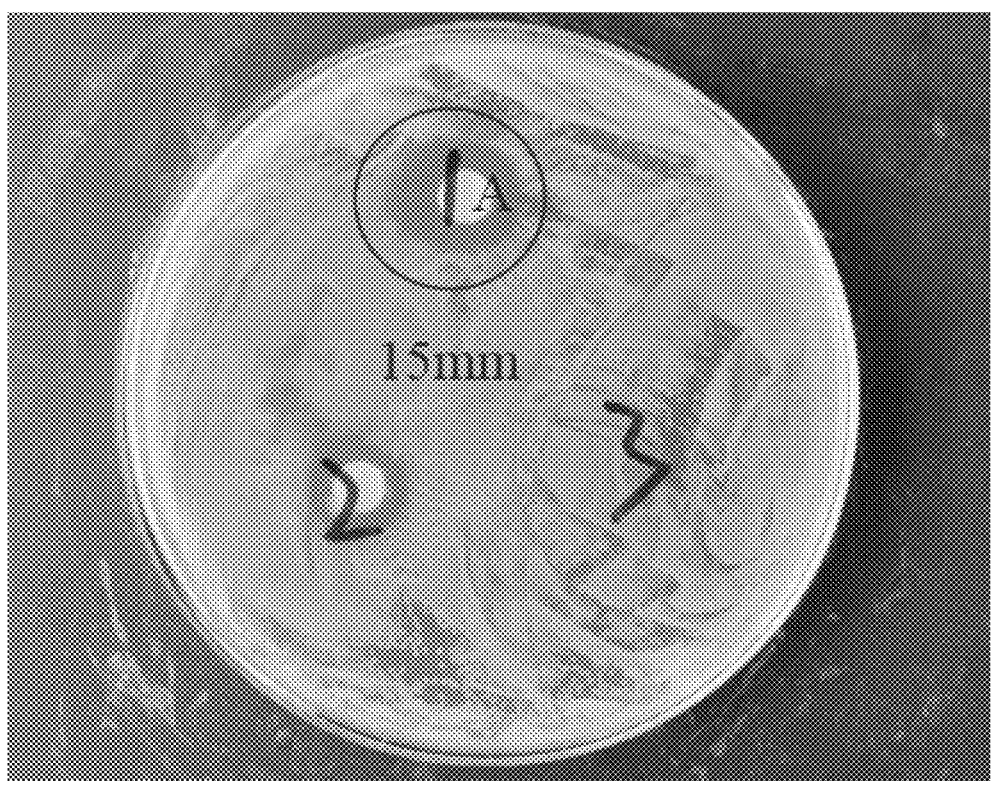
FIG. 3 shows the in vitro antibacterial activity of pleuromutilin (E)-4-(1-imidazoylmethyl)cinnamic acid ester against drug-resistant bacteria MRSA 18-575.

In FIGS. 1-3, pleuromutilin (E)-4-(1-imidazoylmethyl) cinnamic acid ester is represented by the letter A. FIG. 1 shows the antibacterial effect of pleuromutilin (E)-4-(1-imidazoylmethyl)cinnamic acid ester on MRSA 18-171. FIG. 2 shows the antibacterial effect of pleuromutilin (E)-4-(1-imidazoylmethyl)cinnamic acid ester on MRSA 18-222. FIG. 3 shows the antibacterial effect of pleuromutilin (E)-4-(1-imidazoylmethyl)cinnamic acid ester on MRSA 18-575. The results are also shown in Table 1.

TABLE 1

Experimental results of the zone of inhibition

| Compound | Zone of inhibition/mm Strain | | |
|---|---|---|---|
| | MRSA-171 | MRSA-222 | MRSA-575 |
| Vancomycin | 17 | 18 | 21 |
| Pleuromutilin | 0 | 0 | 0 |
| (E)-4-(1-imidazoylmethyl)cinnamic acid | 0 | 0 | 0 |
| Pleuromutilin (E)-4-(1-imidazoylmethyl) cinnamic acid ester | 16 | 17 | 15 |

The results in FIGS. 1-3 and Table 1 show that pleuromutilin and (E)-3-(4((1H-imidazol-1-yl)methyl)phenyl) acrylic acid have no inhibitory effect on drug-resistant bacteria. Pleuromutilin (E)-3-(4((1H-imidazol-1-yl)methyl) phenyl)acrylate derivative has strong inhibitory effects on multi-drug resistant *Staphylococcus aureus* 171, 222, 575, and the diameter of bacteriostatic zone against multidrug resistant *Staphylococcus aureus* 222 was up to 17 mm. In summary, Pleuromutilin (E)-3-(4((1H-imidazol-1-yl) methyl)phenyl)acrylate ester of the present invention can be used as an antibacterial drug candidate for multi-drug resistant *Staphylococcus aureus*, and further preclinical studies will be conducted.

What is claimed is:

1. A compound with anti-drug resistant bacteria activity having the following formula (I):

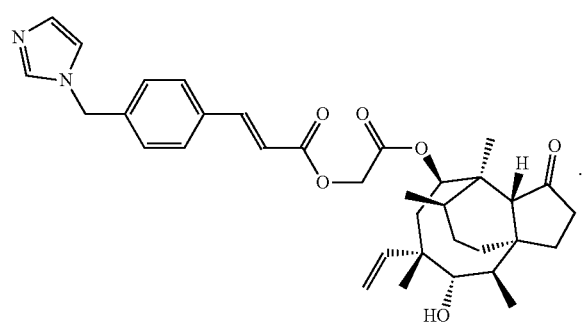

(I)

2. A method of preparing the compound of formula (I) of claim 1, comprising:
reacting a compound of formula (II) with a compound of formula (III) to obtain the compound of formula (I):

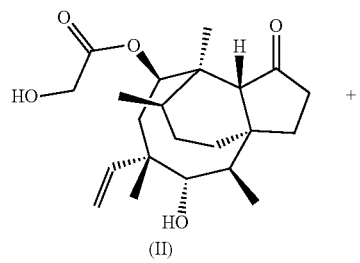

(II)

+

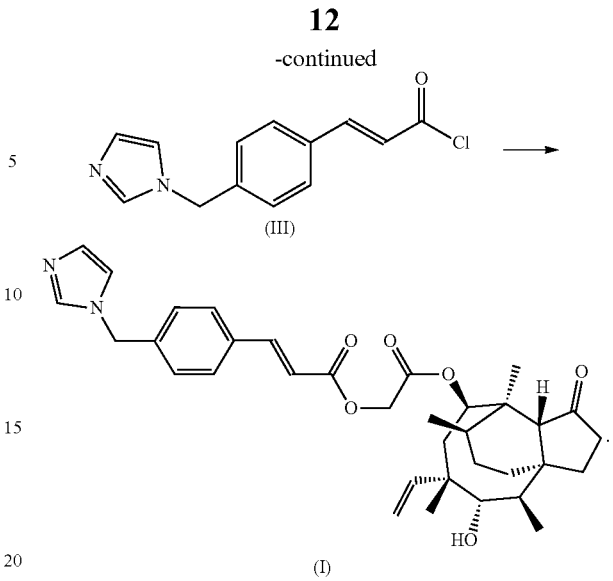

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of triethylamine under nitrogen atmosphere to obtain a reaction mixture;
heating the reaction mixture at 20-60° C. for 3-6 hours;
extracting the reaction mixture with ethyl acetate to obtain a crude product; and
purifying the crude product on a silica gel fresh chromatography column with dichloromethane and methanol as an eluent to obtain the compound of formula (I).

4. The method of claim 3, wherein the organic solvent is toluene, dichloromethane or N,N-dimethylformamide.

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is heated at 25° C.

8. The method of claim 3, wherein the reaction mixture is heated for 5 hours.

9. The method of claim 3, wherein the eluent is dichloromethane:methanol=10:1.

10. A method of preparing the compound of formula (I) of claim 1, comprising:
reacting a compound of formula (II) with a compound of formula (IV) to obtain the compound of formula (I):

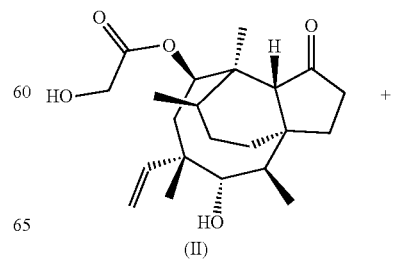

(II)

+

-continued

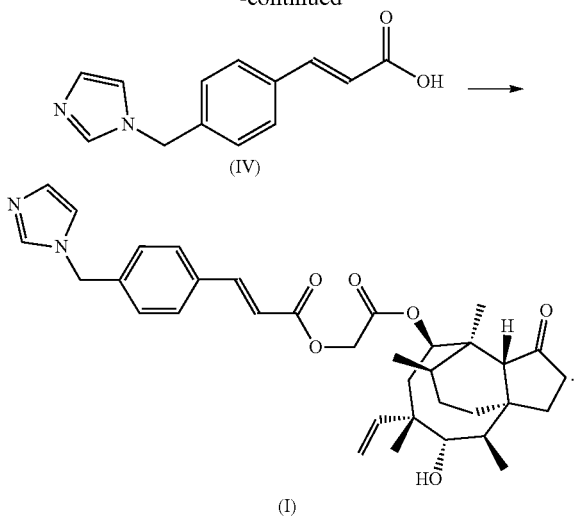

11. The method of claim 10, wherein the reaction of the compound of formula (II) with the compound of formula (IV) comprises the following steps:
  placing the compound of formula (II), a catalyst, and an ionic liquid in a reactor under nitrogen atmosphere, the catalyst being 12-molybdosilicic acid hydrate ($H_6Mo_{12}O_{41}Si$);
  adding the compound of formula (IV) to the reactor to form a reaction mixture;
  heating the reaction mixture at 20-50° C. for 4-8 hours;
  placing the reaction mixture in a separating funnel to separate a crude product;
  purifying the crude product by recrystallization in methanol to obtain the compound of formula (I); and
  recycling the ionic liquid.

12. The method of claim 11, wherein the ionic liquid is 1-octyl-3-methylimidazolium hexafluorophosphate, 1-hexyl-3-methylimidazolium tetrafluoroborate or 1-butyl-3-methylimidazolium tetrafluoroborate ([BMIM][$BF_4$]).

13. The method of claim 11, wherein the ionic liquid is the ionic liquid is 1-butyl-3-methylimidazolium tetrafluoroborate.

14. The method of claim 11, wherein the compound of formula (II) and the compound (IV) have a molar ratio of 1:1 to 1:1.3.

15. The method of claim 14, wherein the molar ratio of the compound of formula (II) and the compound of formula (IV) is 1:1.1.

16. The method of claim 11, wherein the reaction mixture is heated at 30° C.

17. The method of claim 11, wherein the reaction mixture is heated for 6 hours.

* * * * *

UNITED STATES PATENT AND TRADEMARK OFFICE
CERTIFICATE OF CORRECTION

| | | |
|---|---|---|
| PATENT NO. | : 11,510,905 B1 | Page 1 of 1 |
| APPLICATION NO. | : 17/239583 | |
| DATED | : November 29, 2022 | |
| INVENTOR(S) | : Liang et al. | |

It is certified that error appears in the above-identified patent and that said Letters Patent is hereby corrected as shown below:

On the Title Page

Item (71) 2nd Applicant, changed from:
"Wenjing Yang, Xi'an (CN)"
To:
"Wenjing Yan, Xi'an (CN)"

Item (72) 2nd Inventor, changed from:
"Wenjing Yang, Xi'an (CN)"
To:
"Wenjing Yan, Xi'an (CN)"

Signed and Sealed this
Tenth Day of January, 2023

Katherine Kelly Vidal
*Director of the United States Patent and Trademark Office*